United States Patent [19]

Stolowitz

[11] Patent Number: 5,246,865
[45] Date of Patent: Sep. 21, 1993

[54] THIOBENZOYLATION METHOD OF PEPTIDE SEQUENCING WITH GAS CHROMATOGRAPHY AND MASS SPECTROMETRIC DETECTION

[75] Inventor: Mark L. Stolowitz, Long Beach, Calif.

[73] Assignee: California Institute of Technology, Pasadena, Calif.

[21] Appl. No.: 919,524

[22] Filed: Jul. 24, 1992

[51] Int. Cl.$^5$ .................... G01N 30/72; G01N 33/68
[52] U.S. Cl. ........................ 436/89; 436/92; 436/96; 436/161; 436/173; 530/345; 530/410
[58] Field of Search ............. 436/89, 90, 92, 96, 436/161, 173; 530/345, 410

[56] References Cited

U.S. PATENT DOCUMENTS

| | | | |
|---|---|---|---|
| 3,997,298 | 12/1976 | McLafferty et al. | 436/89 X |
| 4,224,031 | 9/1980 | Mee et al. | 436/90 X |
| 4,548,904 | 10/1985 | Kent et al. | 436/89 |
| 4,861,726 | 8/1989 | Stolowitz et al. | 436/89 |
| 4,863,870 | 9/1989 | Stolowitz et al. | 436/89 |
| 5,008,372 | 4/1991 | Wellner | 436/89 X |

OTHER PUBLICATIONS

Previero, A. "Alternative Reagents in Sequential Degradation on Solid Phase Supports" in: Hirs, C. H. W. *Methods in Enzymology*, vol. 47, Part E, pp. 289-299 (1977).

Barrett, G. C. et al. "Thin Layer Chromatography of N-Thiobenzoylamino Acid Analides" Journal of Chromatrography of N-Thiobenzoylamino Acid Analides Journal of Chromatography, vol. 39 (1969) pp. 47-52.

Vance, D. E. et al., "Reaction of Proteins and Peptides with Methyl isothiocyanate and Identification of the Methylthiohydantoins by Gas-Liquid Chromatography" Chemical Abstracts, vol. 73 (1970) No. 5270k.

*Primary Examiner*—James C. Housel
*Assistant Examiner*—Jeffery R. Snay
*Attorney, Agent, or Firm*—Blakely, Sokoloff, Taylor & Zafman

[57] ABSTRACT

A protein microsequencing method for use in conjunction with the thiobenzoylation degradation of polypeptides and proteins is disclosed. The process involves reaction of the N-terminal amino acid of a polypeptide with an excess of a thiobenzoylating reagent. The derivatized polypeptide is subjected to cleavage by acid which forms a 4-substituted 2-phenyl-5(4H) thiazolone. The thiazolone is acylated to form a 5-acyloxy-2-phenylthiazole and subjected to detection by both gas chromatography and chemical ionization mass spectroscopy.

18 Claims, 11 Drawing Sheets

THIOBENZOYLATION METHOD OF PEPTIDE SEQUENCING WITH GAS CHROMATOGRAPHY AND MASS SPECTROMETRIC DETECTION

This invention was made with government support under National Science Foundation Grant Number NSF 8897710.

BACKGROUND OF THE INVENTION

1. FIELD OF THE INVENTION

The present invention relates to a method and apparatus for the sequential degradation of protein or polypeptides using chemical degradation and solid phase sequencing, and more particularly, this invention relates to a novel method for the microsequencing of very small amounts of protein and identification of the resultant amino acid derivatives.

2. ART BACKGROUND

In 1957, P. Edman published a paper which began a new era in field of protein sequencing, enabling eventually the automated sequencing of proteins and peptides in a liquid phase. P. Edman, Acta. Chem. Scand. 10, 761 (1957).

The three step process first involves coupling the N-terminal amino acid of a starting polypeptide to phenylisothiocyanate (PITC) in the presence of an acid scavenger in an alkaline aqueous or anhydrous solvent. The volatile excess reagent is removed in vacuo (homogeneous phase reaction) or by washing a polypeptide immobilized on an insoluble support (heterogeneous phase reaction) and byproducts of the reaction resulting from the decomposition of PITC are similarly removed, to yield the phenylthiocarbamyl (PTC) polypeptide.

In the second step, the PTC polypeptide is subjected to cleavage by a volatile anhydrous acid to afford the 2-anilino-5(4H)-thiazolone (ATZ) of the N-terminal amino acid and the salt of the residual polypeptide, which is the starting polypeptide with the N-terminal amino acid removed.

The ATZ amino acid is extracted from the residual polypeptide or washed from the insoluble support in the cleavage acid which is subsequently removed in vacuo or evaporated under a stream of nitrogen gas at elevated temperature. In the third step, the ATZ amino acid, is ordinarily subjected to conversion to the more stable phenylthiohydantion (PTH) amino acid. The conversion reaction can be effected thermally or by heating the ATZ amino acid in aqueous, methanolic or anhydrous acid.

The resultant PTH amino acid is identified chromatographically while the shortened residual polypeptide is reacted with PITC to initiate the next cycle of degradation. The foregoing steps (coupling, cleavage and conversion) are repeated for each N-terminal amino acid in the polypeptide.

In 1967 Edman taught in, Edman et al., "A Protein Sequenator" European J. Biochem. 1 (1967) 80–91 a "spinning cup" automated sequencer which permitted the automated sequencing of peptides, still using a liquid phase separation.

In the late 1960's and early 1970's, a modification of the basic Edman chemistry was developed which involved the concepts of Edman degradation as applied using solid phase chemistry. These developments, pioneered by Richard Laursen, Eur. J. Biochem 20 (1971) 89–102 "Solid Phase Edman Degradation-An Automatic Peptide Sequencer" enabled researchers to bind the protein or peptide to be sequenced onto a solid resin, and to pump the Edman reagents past the bound peptide to provide the chemistry that sequentially degraded the peptide.

For background, it is relevant to review the Edman and thioacylation degradation techniques.

THIOACYLATION

The thioacylation degradation of proteins and polypeptides was first proposed by Barrett (Barrett, G. C. (1967) Chem. Comm. 487) as an alternative to the Edman degradation. The process involves reacting the N-terminal amino acid of a starting polypeptide immobilized on an insoluble support by adsorption or covalent attachment with a thioacylating reagent. The excess reagent is washed away to yield the N-thioacyl polypeptide, Formula A, wherein X is a hydrogen or some other reactivity modifying group, and R represents the various amino acid side chains.

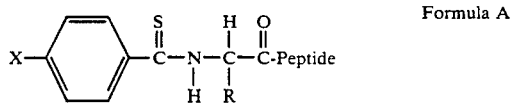

Formula A

In the second step, the thioacyl polypeptide is subjected to cleavage by volatile anhydrous acid to form a 2-substituted-5(4H)-thiazolone of the N-terminal amino acid, formula B. Thioacylation offers some advantages over the Edman degradation in that the cleavage reaction is short in duration and occurs under relatively mild conditions. Also liberated during the cleavage reaction is the salt of the residual polypeptide, which is the starting polypeptide with the N-terminal amino acid removed.

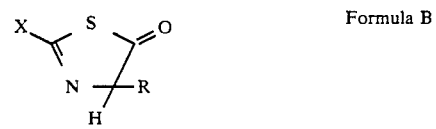

Formula B

The 2-methyl-5(4H)-thiazolones were historically identified after regeneration of the free amino acids by acid hydrolysis (Mross, G. A. and Doolittle, R. F. (1971) Fed. Proc. 30, 1241. Mross, G. A. and Doolittle, R. F. (1977) in Advanced Methods in Protein Sequence Determination (Needleman, S. B., ed.) pp. 1-20, Springer, Heidelberg). Consequently, cysteine, serine, threonine and tryptophan were not recovered in high yield as a result of their instability during hydrolysis and the amide moieties of asparagine and glutamine were hydrolyzed to the corresponding acids. Therefore, the identification of the foregoing species becomes impossible using this methodology. 2-Methyl-5(4H)-thiazolones have also been identified by gas liquid chromatography, preferably, after reaction with excess acetic anhydride in pyridine or acetyl chloride in trifluoroacetic acid (TFA) (Previero, A. (1977) in Methods in Enzymology (Hirs, C. H. W. and Timasheff, S. N., eds.) Vol 47, Part E, pp. 289-299, Academic Press, New York) which yields the corresponding 5-acetoxy-2-methyl-thiazoles, Formula C

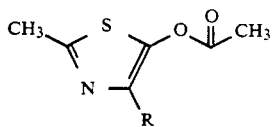

Formula C

2-Phenyl-5(4H)-thiazolones, resulting from the thiobenzoylation degradation have been identified directly by electron impact mass spectrometry and by thin layer chromatography after conversion to the corresponding N-thiobenzoyl amino acid anilides (Barrett, G. C. and Khokhar, A. R. (1969) J. Chromatog. 39, 47). Gas chromatographic analysis of 2-phenyl-5(4H) thiazolones and 5-acetoxy-2-phenylthiazoles has not been reported, and it had been assumed by analogy to PTH amino acids that they lacked adequate volatility for gas chromatographic analysis.

Various reagents including S-(carboxymethyl) dithiobenzoate (CMBTB), S-(cyanomethyl dithiobenzoate, m-nitrobenzoylthionocholine and N-thiobenzoylsuccinimide have been proposed for the sequential degradation of polypeptides by the thioacylation method. Several of aforementioned compounds are not as reactive as PITC and this constituted an important drawback for the development of a satisfactory procedure for sequential analysis. Of the aforementioned reagents CMBTB has been utilized the most extensively.

The emphasis at the present time is on the development of chemistries and apparatus which is substantially more sensitive, faster and in some instances, less expensive that prior art systems. The first parameter of sensitivity is particularly critical since many of the prior art methods are not entirely satisfactory in the microsequencing of quantities of protein less than 10 picomoles.

Many physiologically active proteins are present in organisms at such extremely small concentrations that only very small amounts of the proteins can be obtained for sequencing analysis. The current techniques described in the literature are aiming to obtain sensitive detecting in the picomole range. Hunkapiller and Hood, "Protein Sequence Analysis: Automated Microsequencing", Science 219 (1983) 650-659 teaches automated sequencing in the 5 to 10 picomole range.

Inman and Appella, "Newer Methods of Solid-and Liquid Phase Sequence Determination-Personal Views," *Practical Protein Chemistry-A Handbook*, A. Darbre, Editor (1986), describe the state of the art of protein microsequencing including a discussion of the known chemical protein degradation methodologies using solid phase sequencing, namely Edman degradation, thioacylation and acid cleavage, and C-terminal degradation. With respect to thioacylation chemistry, the authors describe the prior work of Barrett and others, noting that they proposed methods of sequential degradation based on the coupling of a thioacyl group, to the N-terminal amino function of a peptide followed by acid cyclization and cleavage of the terminal residue as a thiazolone derivative. The primary advantages of this chemistry over the standard Edman chemistry is that the cyclization and cleavage occur under less drastic conditions. Specifically, treatment with TFA (trifluoracetic acid) at room temperature or slightly higher temperatures for 20 minutes, or even weaker acids at slightly higher temperatures may be employed, which is substantially milder than the current standard Edman chemistry. As a result, damage to peptide or protein prior to completion of the sequencing can be minimized. The authors note that the development of this methodology has been limited by the availability of thioacylating reagents which are as efficient in the coupling step as phenylisothiocyanate. Specifically, the authors have noted, in table 16.1, that the following thioacylating agents have been used in the prior art:

TABLE 16.1

Thioacylating agents with general structure R-C(=S)-X used for studying sequential degradations for peptides:

| Item | Acyl Substituent R | Leaving Group X |
|---|---|---|
| 1 | phenyl | —SCH$_2$COO— |
| 2 | phenyl | —SCH$_2$CN |
| 3 | phenyl | —CH$_2$OCH$_3$ |
| 4 | phenyl | 4-nitrophenolate |
| 5 | phenyl | succinimidyl |
| 6 | m-nitrophenyl | OCH$_2$CH$_2$N + (CH$_3$) |
| 7 | methyl | —SCH$_2$COO— |
| 8 | methyl | —SCH$_2$CH$_3$ |
| 9 | methyl | —SCH$_3$ |
| 10 | ethyl | —SCH$_3$ |
| 11 | propyl | —SCH$_3$ |
| 12 | isopropyl | —SCH$_3$ |

In "Reactions of α-Thioacylamino-acids. Their Conversion into Thiazolones and Derivatives Thereof," Jepson, Lawson and Lawton, J. Chem Soc. (1955) 1791-1797, the thioacylation of amino acids to form thiazolones (N-thiobenzoyl-Formula E) was first studied and reported, as depicted below:

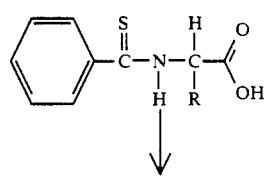

Formula D

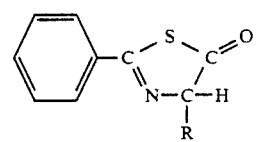

Formula E

Barrett in 1967 in "Cleavage of N-Thiobenzoyl-dipeptides with Trifluoroacetic Acid: the Basis of a New Stepwise Degradation of Polypeptides" *Chemical Communications*, (1967) 487 proposed thiobenzoylation as an alternative to Edman degradation. In 1968, Barrett reported that the cleaved N-terminal amino acid could be detected by mass spectrometry. *Chemical Communications*, (1968) 335. In 1969, Barrett reported that N-thiobenzoyl amino acid anilides could be detected by thin layer chromatography. J. Chromatog. 39 (1969) 47-52.

The present invention attempts to overcome some of the problems with the prior art chemistry for sequencing peptides and proteins by providing a method of sequencing using thiobenzoylation which permits detection of the resultant derivatized thiazolone amino acid by gas chromatography and mass spectroscopy.

SUMMARY OF THE INVENTION

The present invention affords a number of advantages over the prior art Edman and thioacylation and thioacetylation degradations including the following:

i) the reagents utilized in the present invention are generally commercially available, whereas many of the reagents in the prior art had to be specially synthesized, and the reagents are crystalline solid substances having no appreciable odor associated with it, as compared with the prior art thioacetylation reagents;

ii) the reagents of the present invention are more hydrophobic than the reagents used in the thioacetylation, enabling them to be retained by the typically used polyvinyldine difluoride (PVDF) hydrophobic membranes so that the protein or peptide sample may be applied to the membrane as thin film;

iii) the reagents used herein are more reactive (20-50 times) than the reagents of thioacetylation reactions;

iv) the enol to keto equilibrium favors the enol form due to the hyperconjugation (aromaticity) of the resultant molecule, making the derivatization reaction faster and enabling it to go to completion under milder conditions than the thioacetylation method; and v) the analytical standards (used for calibration) are easier to prepare and more stable, and are more easily crystallized than the prior art standards.

The present invention is a method of sequencing proteins and peptides by thiobenzoylation of the protein or peptide, followed by cleavage, and then conversion to a detectable and stable species. The method of the present invention permits the rapid and sensitive detection of the amino acids of the peptide or protein to be sequenced. The method and chemistry involved also permits the resultant derivative amino acid to be detected independently, or preferably sequentially, by gas chromatography and mass spectroscopy, and specifically and preferably, by chemical ionization mass spectrometric detection.

In the first step of the present invention, the peptide or protein is bound to a solid support. In the second step, the bound peptide is reacted with a reagent of the general formula:

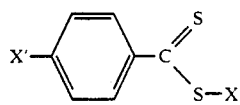

wherein X is an electron withdrawing group, preferably but not limited to the groups selected from —CH$_2$COOH, —CH$_2$CN, —CH$_2$COOCH$_3$ and —CH$_2$OCH$_3$, and X' is a reactivity modifying substituent whereby the reactivity of the reagent is increased when X' is electron withdrawing and the cleavage conditions for the thioacylpeptide become less drastic when X' is electron donating. X' is preferably selected from —NO$_2$, —CN, —CH$_3$, —OCH$_3$, —SO$_3$.

Most preferably, the reagent of choice at this time is S(carboxymethy)dithiobenzoate having the following formula II:

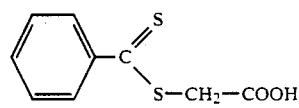

The thiobenzoylation reaction occurs in the presence of 1% to 10% triethylamine (TEA) or similar reagent such as N-methylmorpholine in a solution containing up to 50% organic alcohol or acetonitrile at from 40° to 75° C., at a prescribed rate of about 25-250 µl per minute to avoid washing the peptide off the membrane support but enable the reaction to go to completion.

An N-thiobenzoyl peptide of the following general formula is formed.

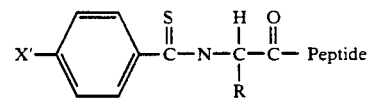

The resultant peptide is then treated with a cleavage reagent, and preferably a perfluorinated carboxylic acid or an anhydrous hydrochloric acid, and more preferably trifluoroacetic acid (TFA), pentafluoropropionic acid, and heptafluorobutyric acid, or 4N HCl in dioxane or 1N HCl in diethyl ether. The cleavage reagent cleaves the N-terminal amino acid from the remaining peptide. The TFA or other cleavage reagent may be in liquid or vapor form. The reaction product of the TFA cleavage is shown below

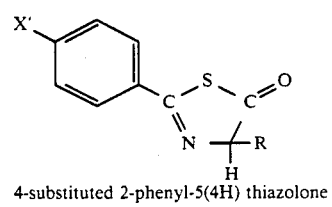

4-substituted 2-phenyl-5(4H) thiazolone

This compound exists in a tautomeric equilibrium between the enol and keto forms as a 2-phenyl-5(4H) thiazolone and a corresponding 5-hydroxy-2-phenyl thiazole as shown below:

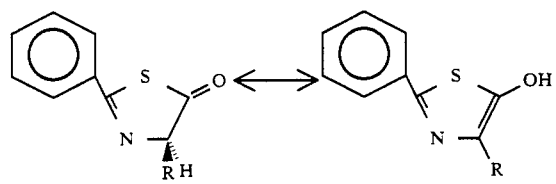

The direction of equilibrium between these two forms is influenced by the solvent polarity, wherein the enol form is favored by more polar solvent, and the keto is favored in the presence of less polar solvents. The direction of equilibrium is also influenced by the acidity of the 4H proton, which is in turn influenced by the substituent at the 2-position of the thiazole ring. For the 2-phenyl-5(4H)thiazolones, the enol form is further favored by hyperconjugation and the aromaticity of the resulting 2-phenylthiazole ring system.

The resultant amino acid derivative is then treated with an acylating agent such as acetic anhydride, trifluoroacetic anhydride (TFAA), pentafluoropropionic anhydride (PFAA), or heptafluorobutyric anhydride (HFBAA) or similar reagent or combinations thereof to form a 5-acyloxy-2-phenylthiazole derivative having the general formula:

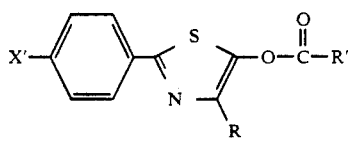

wherein R is the amino acid side chain and R' is selected from $CH_3$, $CF_3$, $CF_2CF_3$ and $CF_2CF_2CF_3$ and is preferably $CH_3$ or $CF_3$.

The preferred acetylating agent is a 7:2:1 combination of acetonitrile:TEA:acetic anhydride. This derivative is subject to detection and identification by gas chromatography which can identify the subject amino acid. The derivative may subsequently be further identified by mass spectroscopy, and particularly, by chemical ionization mass spectroscopy.

The 5-acyloxy-2-phenylthiazole is concentrated by evaporation in vacuo or dried under a stream of argon or nitrogen gas and then dissolved in an aprotic organic solvent preferably selected from either ethyl acetate, hexane or acetonitrile and containing up to 30% by volume TEA and injected into a gas chromatography/mass spectrometer equipped with chemical ionization detection. Chemical ionization reagent gases suitable for analysis of amino acid derivatives of the present invention are selected from ammonia, methane, methanol and isobutane and is preferably isobutane.

The 5-acyloxy-2-phenylthiazole is introduced as a vapor into the ionization chamber of the mass spectrometer wherein it collides with reagent gas ions to produce, by proton transfer, 5-acyloxy-2-phenylthiazolium ions of the general formula:

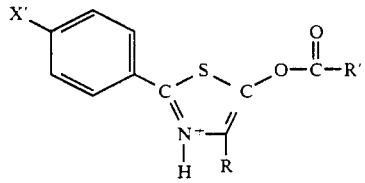

which are detected by the mass spectrometer.

When isobutane is utilized as chemical ionization regent gas very limited fragmentation of the thiazolium ions results, thereby maximizing detection by generating a single molecular ion. More aggressive chemical ionization reagent gasses cause fragmentation which is detected as loss of acetyl moieties. This phenomena reduces detection limits but can provide diagnostic sets of ions which differ by the loss of one, two or three acetyl moieties (as determined by substituents characteristic of the various amino acid side-chains).

As the thiazolium compounds may be resolved by capillary gas chromatography, each amino acid derivative has its own characteristic GC retention time which permits isomers of identical mass (such as leucine and isoleucine, and glutamine and lysine) to be differentiated.

A novel protein microsequencing method for use in conjunction with the thiobenzoylation degradation of polypeptides and proteins is disclosed.

It is an object of this invention to provide a peptide sequencing system capable of sequencing amounts of proteins or peptides in a low picomole or sub-picomole range.

It is another object of this invention to provide a peptide sequencing system capable of detection of sequencing products in a low femtomole or sub-femtomole range.

It is another object of this invention to provide a peptide sequencing system wherein the products of the sequential degradation may be analyzed by either gas chromatography or mass spectroscopy, or preferably both.

It is another object of this invention to provide a peptide sequencing system wherein the products of the sequencing system may be identified by both gas chromatographic retention times and mass spectra thereby enabling the differentiation of isomeric amino acids (leucine and isoleucine).

It is another object of this invention to provide a peptide sequencing system wherein modified amino acid residues, such as methylated, acetylated and glycosylated resides, can be identified.

It is another object of the present invention to provide a method for preparing an amino acid derivative which is suitable for identification by GC and MS.

It is another object of the present invention to provide a method for preparing an amino acid derivatives which have suitable volatilities for GC and GC/MS analysis.

DETAILED DESCRIPTION OF THE PREFERRED EMBODIMENT

EXAMPLE I

Figure 1:
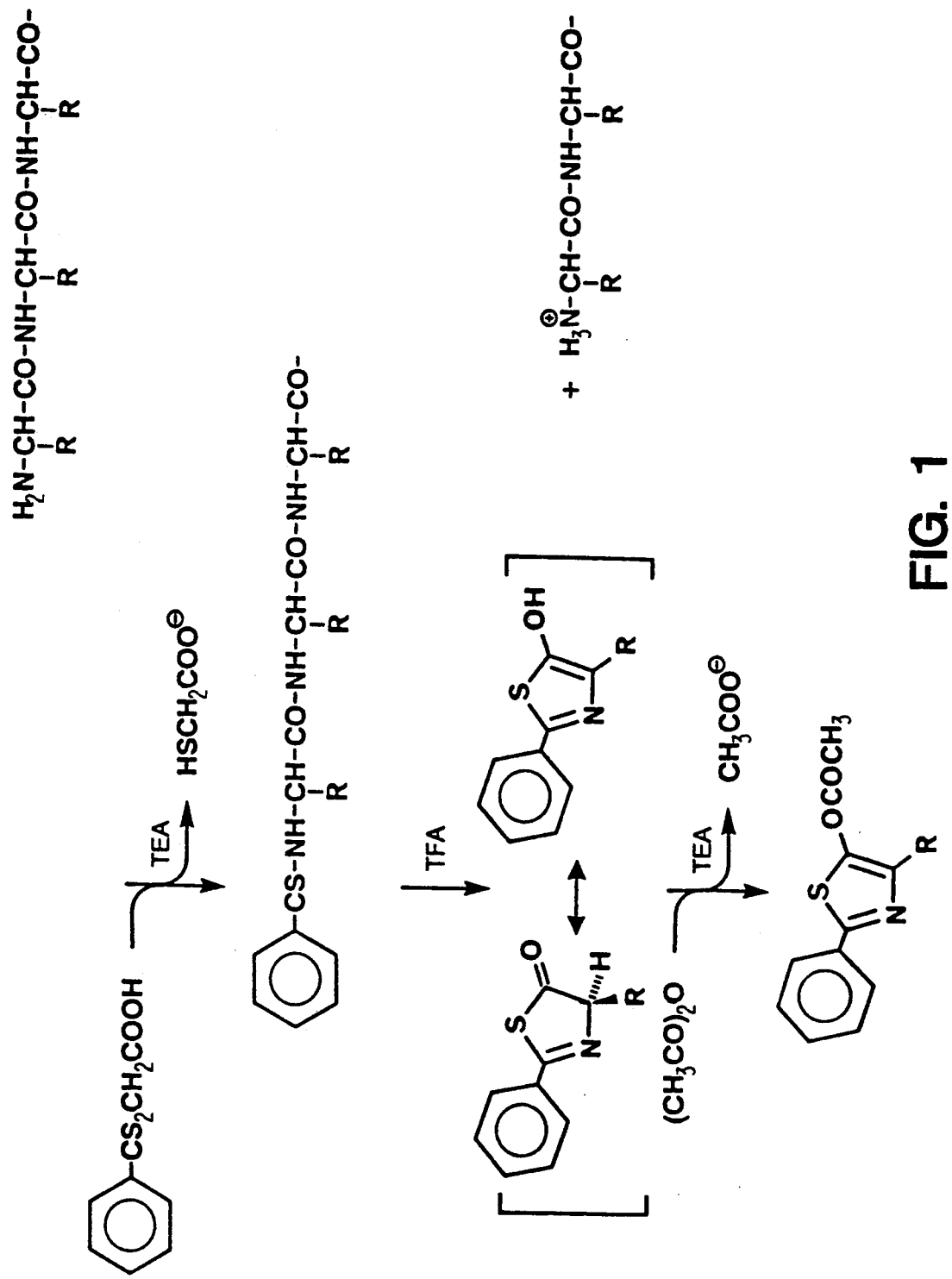
FIG. 1 is a step diagram illustrating the thiobenzoylation method of protein sequencing.
Figure 2:
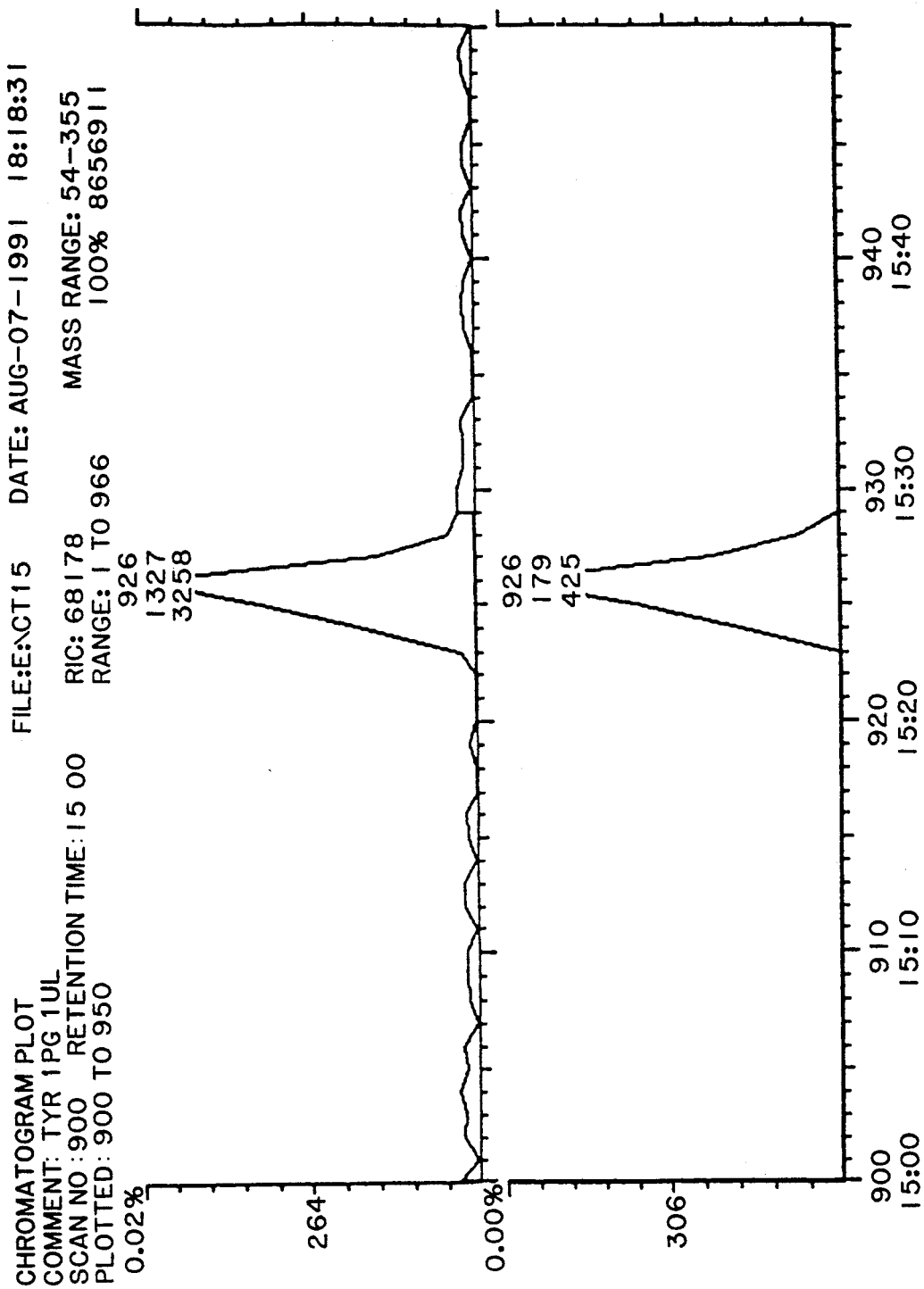
FIG. 2 is a chromatogram plot illustrating the detection of 1 picogram (3.8 femtomole) of a tyrosine standard. Note the detection of both characteristic ions. Optimization of chemical ionization related parameters (and possibly the use of a softer ionizing gas) to minimize fragmentation should afford even greater sensitivity.
Figure 3:
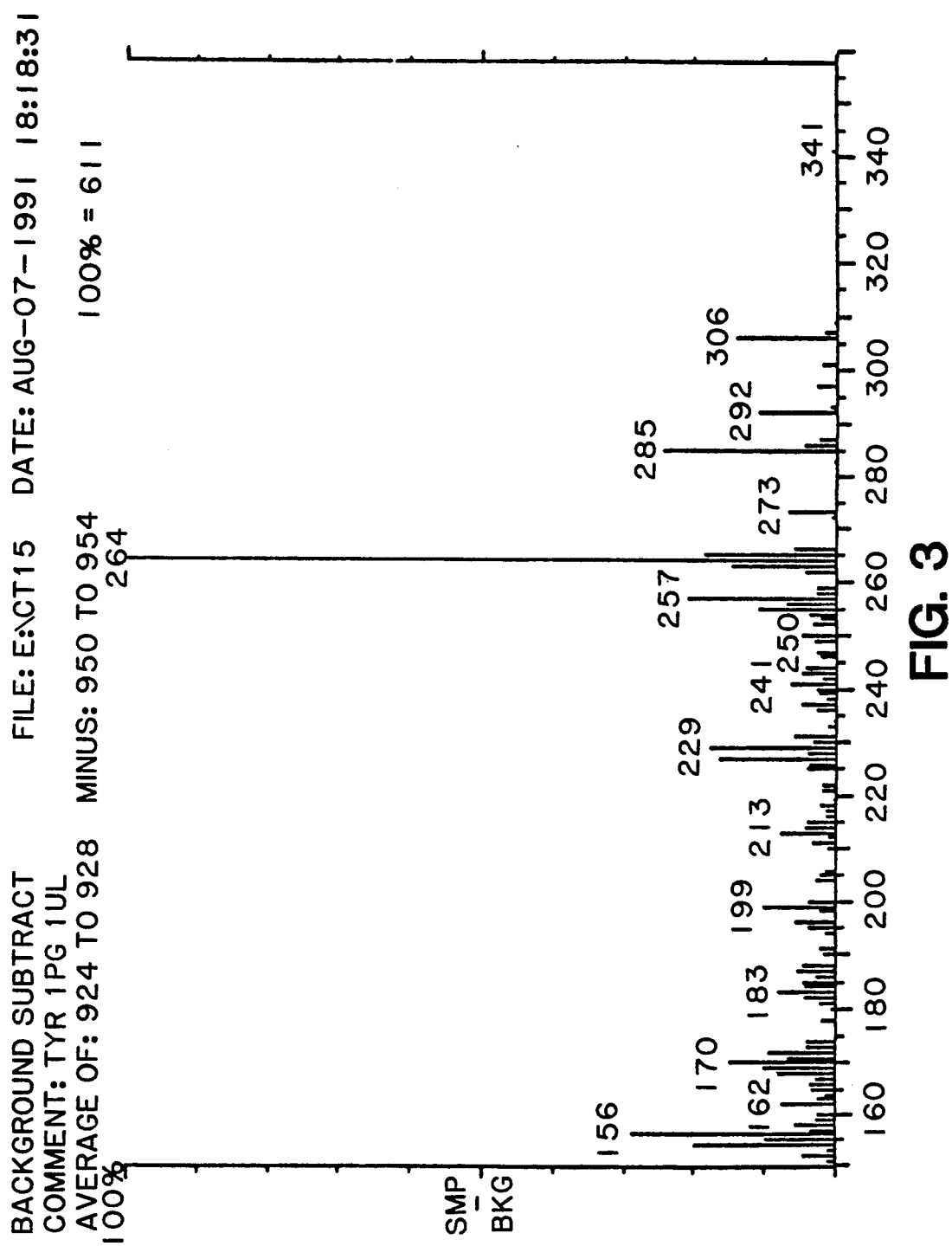
FIG. 3 is a mass spectra illustrating the corresponding mass spectrum of the tyrosine standard of FIG. 2. Similar detection limits were obtained for each of the standards.
Figure 4:
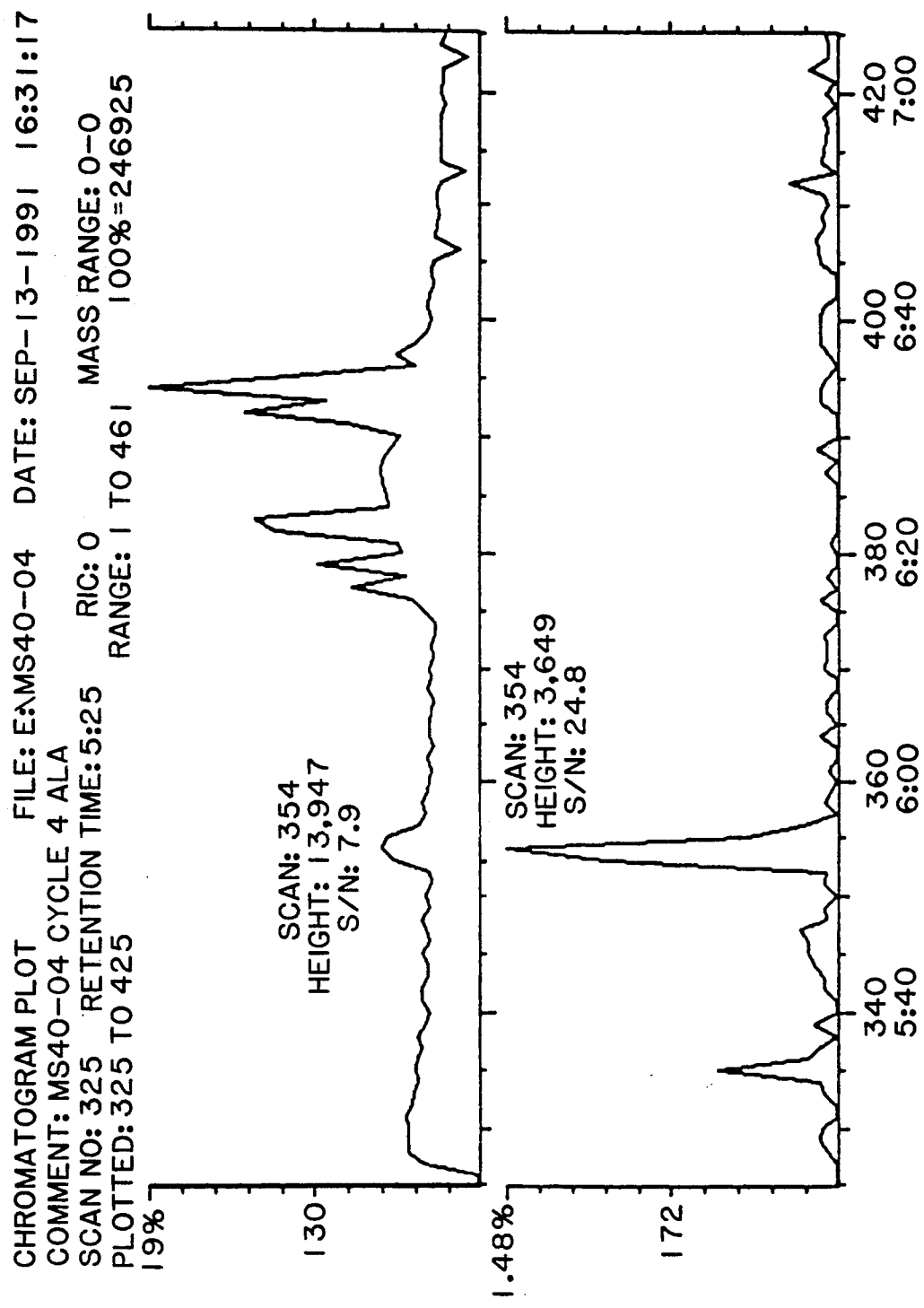
FIG. 4 is a chromatogram plot illustrating the detection of an alanine residue obtained in cycle 4 of a solid-phase thioacetylation degradation of a synthetic peptide MS40 covalently linked to a DITC-PVDF membrane (MilliGen/Biosearch). The initial yield was estimated from cycle 1 to be <0.5 picomole. Only 1/20th of the sample was analyzed. Alanine was selected for illustration as it is the most volatile of the analytes because it must be detected in the presence of other low molecular weight volatile compounds.
Figure 5:
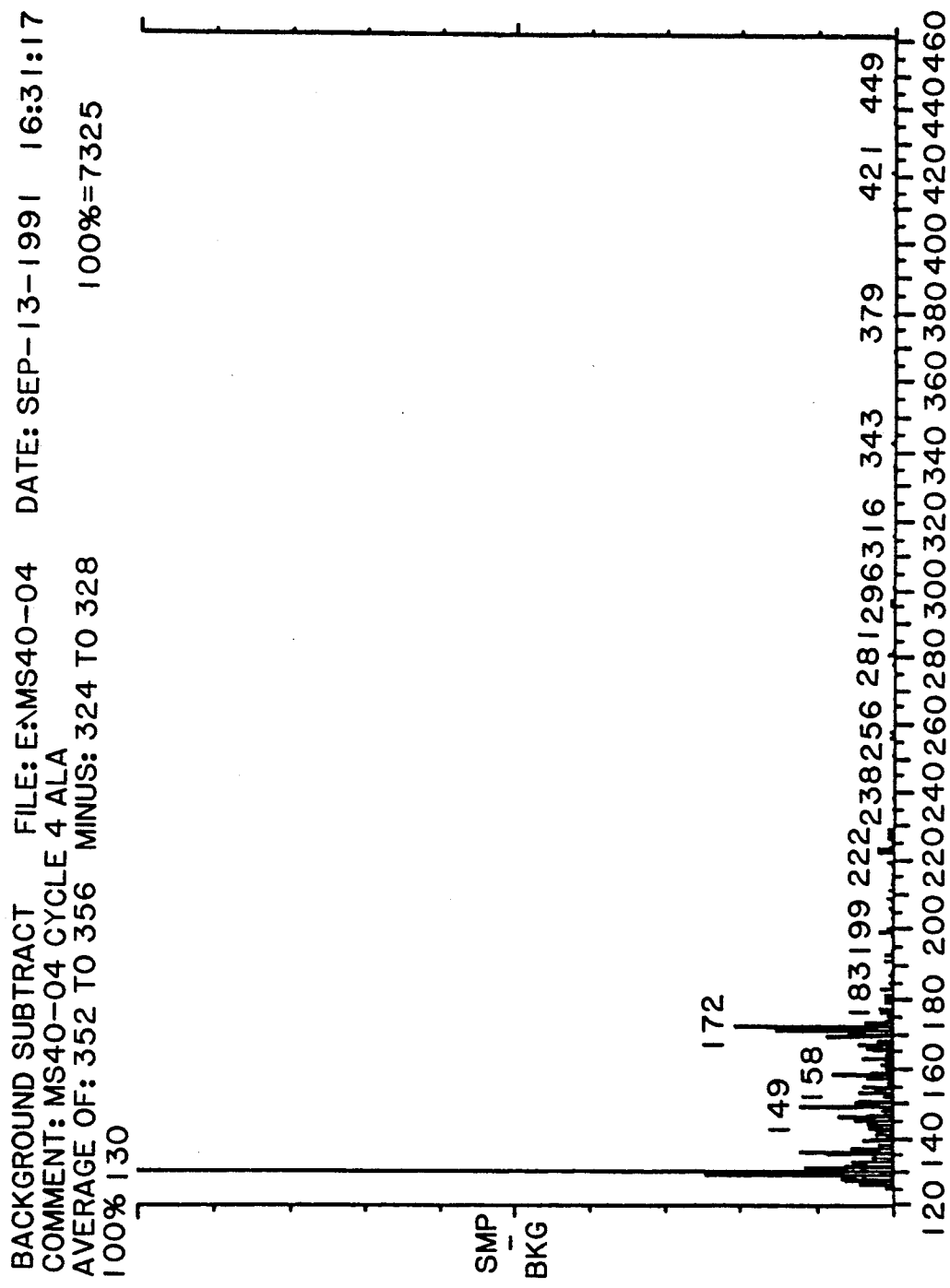
FIG. 5 is a mass spectra illustrating the corresponding mass spectrum of the alanine residue of FIG. 4. Note the detection of both characteristic ions.
Figure 6:
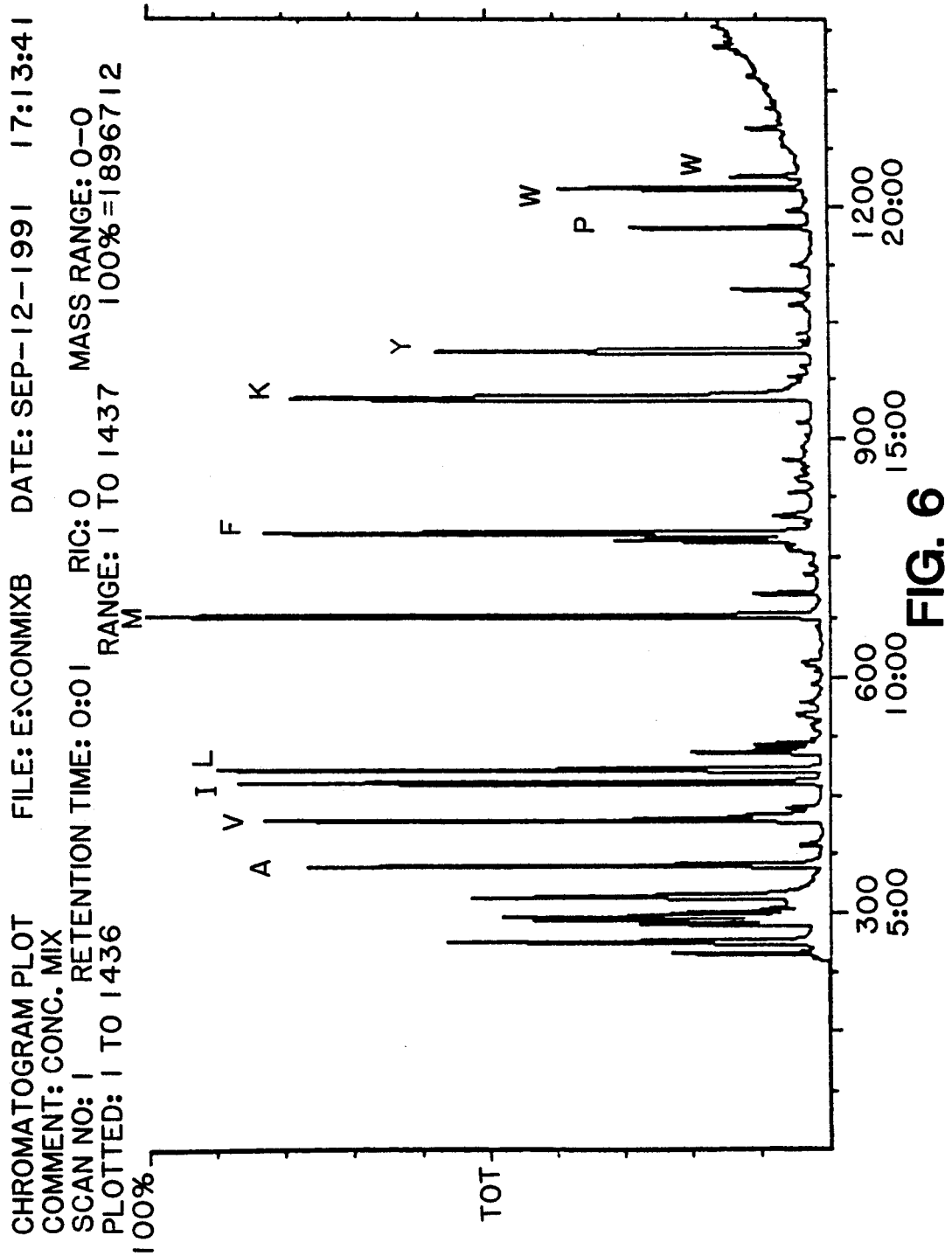
FIG. 6 is a chromatogram plot illustrating the gas chromatographic separation of 10 hydrophobic 5-acetoxy-2-methylthiazole standards on a 0.25 mm I.D., DB-5 capillary column (J and W) of 30 meter length. Note that leucine and isoleucine are differentiated.
Figure 7:
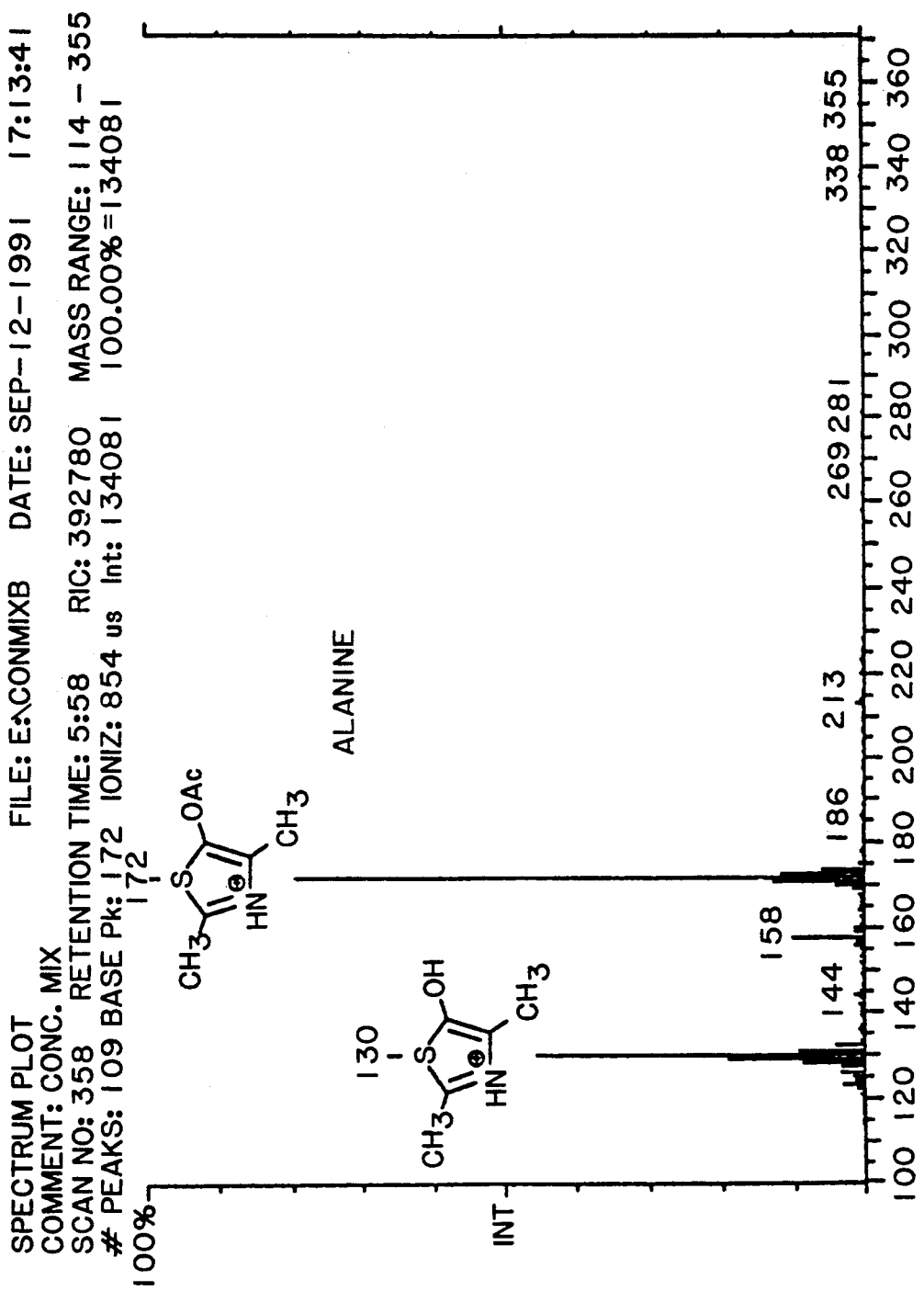
FIG. 7 is a mass spectra illustrating the mass spectrum obtained for the 5-acetoxy-2,4-dimethylthiazole (Ala) standard with methane chemical ionization (CI). The base beak is associated with the acetoxy-thiazolium ion. Chemical ionization induced fragmentation also produced the corresponding hydroxythiazolium ion. These two characteristic ions were obtained for all standards.
Figure 8:
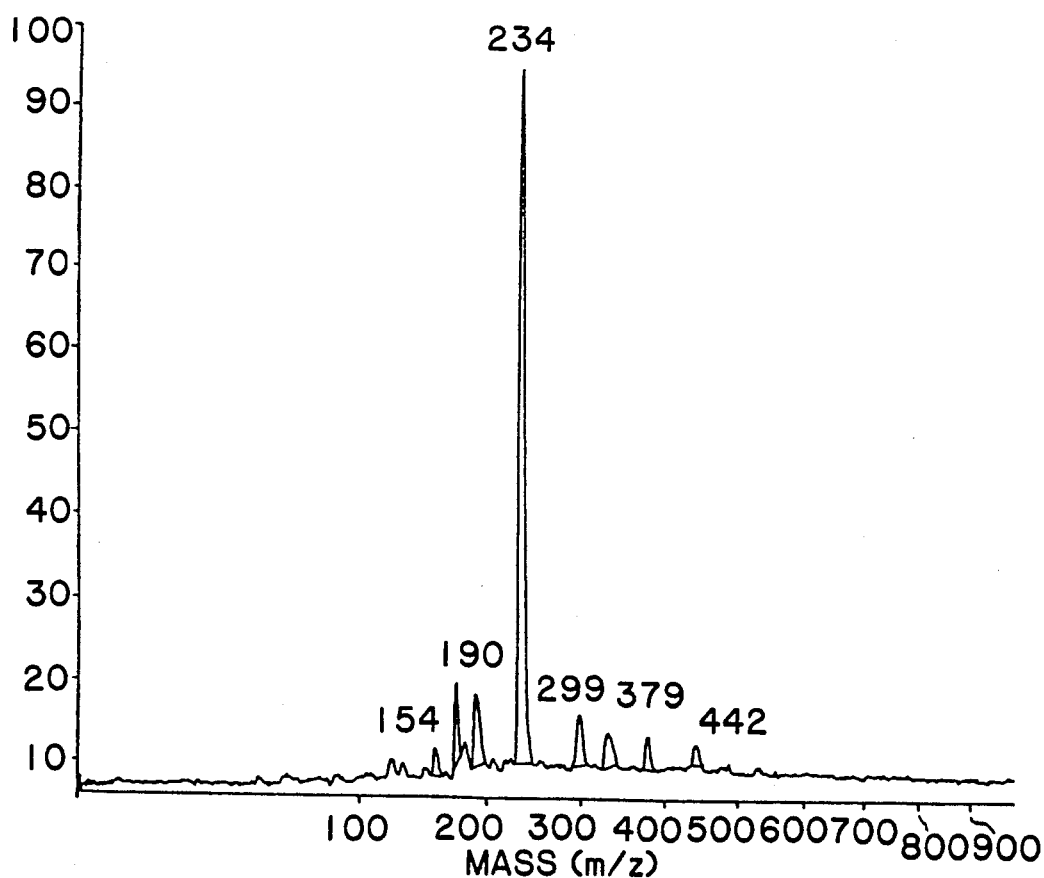
FIG. 8 is a laser desorption time-of-flight mass spectra of the 5-Hydroxy-2-phenylthiazolium ion of leucine in accordance with the present invention.
Figure 9:
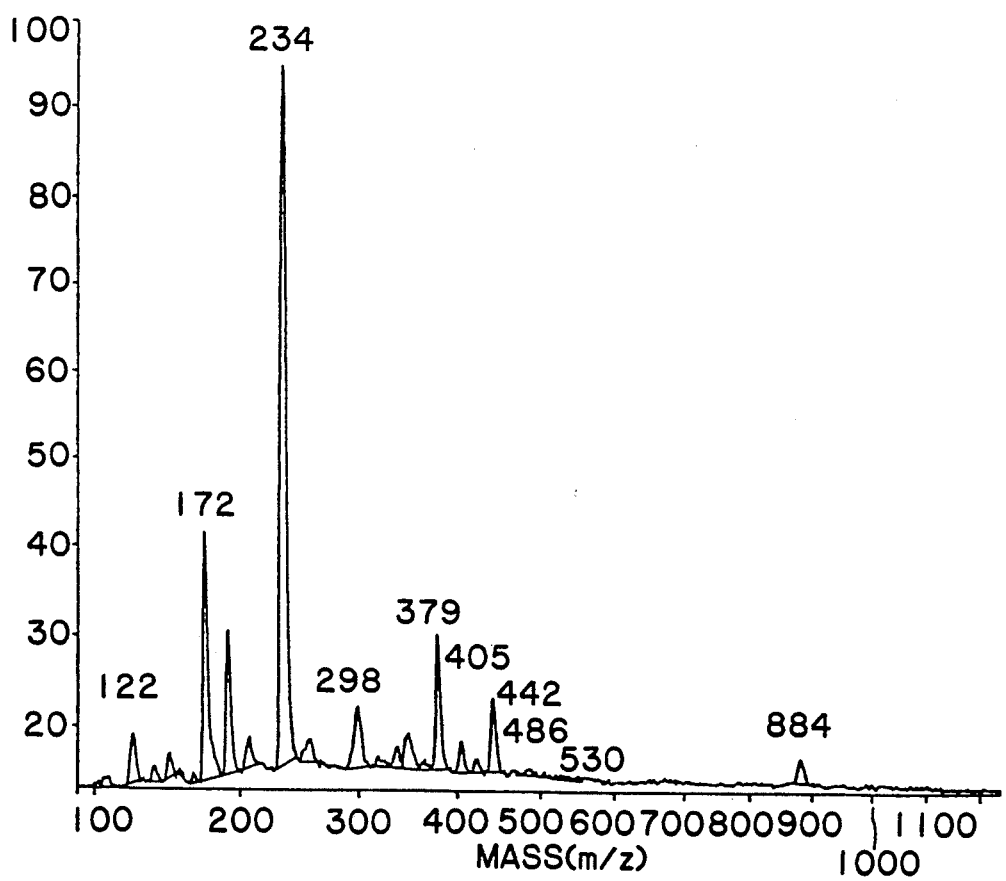
FIG. 9 is a laser desorption time-of-flight mass spectra of the 5-Hydroxy-2-phenylthiazolium ion of isoleucine in accordance with the present invention.
Figure 10:
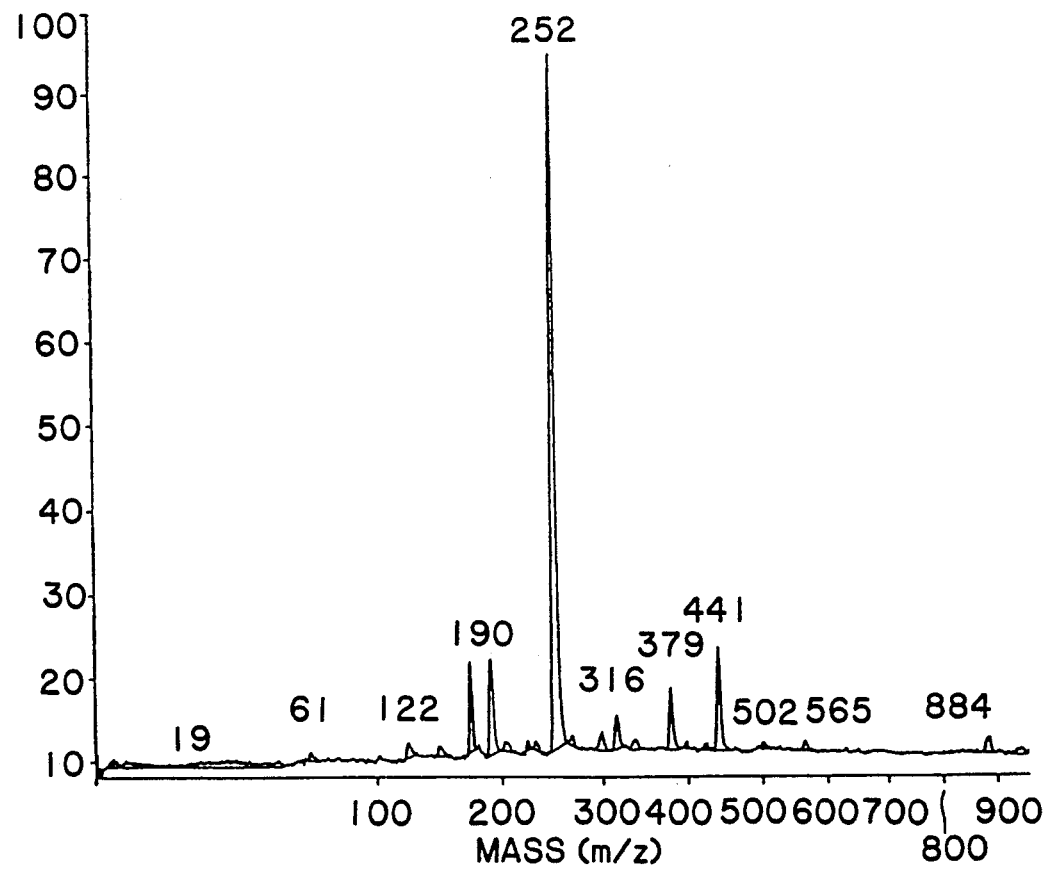
FIG. 10 is a laser desorption time-of-flight mass sprectroma of the 5-Hydroxy-2-phenylthiazolium ion of methionine in accordance with the present invention.
Figure 11:
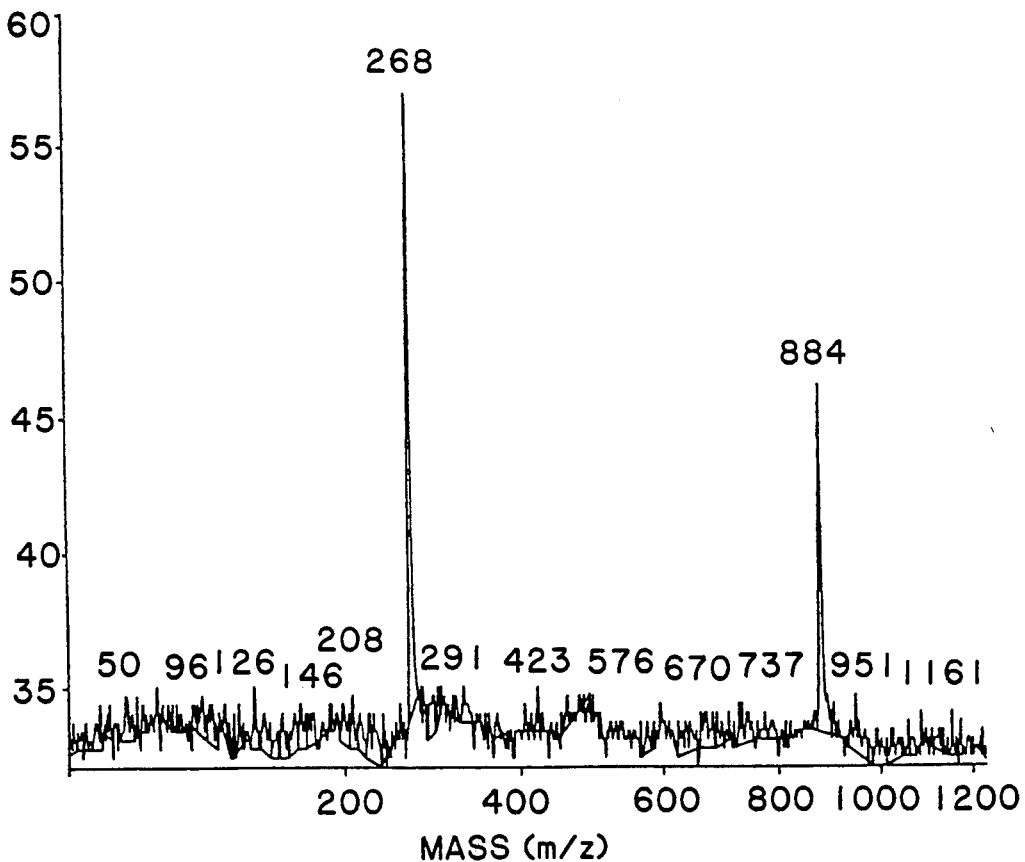
FIG. 11 is a laser desorption time of flight mass spectrometry plot of the 5-Hydroxy-2-phenylthiazolium ion of phenylalanine in accordance with the present invention.

Preparation of N-Thiobenzoylamino-acids. Solutions of S-(carboxymethyl)dithiobenzoate (0.005 mole) in tetrahydrofuran (10 mL) and of amino acid (0.005 mole) in 1N sodium hydroxide solution (10 mL) were stirred and ethanol added dropwise until solution was obtained. The resulting solution was then stirred overnight at room temperature. Additional equivalents of sodium hydroxide solution were added when amino acid hydrochlorides (histidine and lysine) were used, or when the amino acid side-chain included an acidic moiety (aspartic acid, glutamic acid and tyrosine). The reaction was monitored by the change in orange color toward yellow. Upon completion, the solution was acidified to approximately pH 2.0 and the product extracted into ethyl ether. Ethereal extracts were combined, washed throughly with water, and then dried over anhydrous $MgSO_4$. The extract was concentrated in vacuo to obtain the impure N-thiobenzoylamino acids in yields of approximately 90%. Products were obtained as both crystalline compounds and oils, and were often contaminated with traces of S-(carboxymethyl)dithioacetate and mercaptoacetic acid. Chromatographic purification on silica gel employing 97:3 chloroform:isopropanol as eluent was occasionally utilized when products of high purity were desired. Insoluble derivatives of histidine and lysine were precipitated upon acidfication of the reaction. N-thiobenzoylarginine precipitated upon formation and was recovered by filtration. In most instances, impure N-thiobenzoylamino acids proved satisfactory for subsequent reactions.

EXAMPLE II

Preparation of 5-Hydroxy-2-phenylthiazolium Hydrochlorides. N-thiobenzoylamino acids (approx. 0.005 mole) prepared as described above were dissolved in anhydrous 4N HCl in dioxane (25 ml) and allowed to stand overnight at room temperature. 5-Hydroxy-2-phenylthiazolium hydrochlorides were precipitated from solution by addition of 5 volumes of cold diethylether. The precipitate was collected on a medium porosity glass sinter funnel, washed with cold ether, and dried overnight in vacuo. The products were analyzed by matrix assisted laser desorption time-of-flight mass spectrometry (LD-TOF-MS) on a Finnigan MAT LaserMAT mass spectrometer employing alpha-cyano-4-hydroxycinnamic acid as matrix. The following masses were determined experimentally for 5-hydroxy-2-phenylthiazolium ions.

| | 5-Hydroxy-2-Phenylthiazolium Ions Detected by Matrix-assisted Laser Desorption Time-of-Flight Mass Spectrometry | | |
|---|---|---|---|
| R | Formula | Formula Mass | Experimental Mass |
| G Gly | $C_9H_8NOS$ | 178.23 | 178 |
| (C),(S) δAla | $C_{10}H_8NOS$ | 190.24 | 190 |
| A Ala | $C_{10}H_{10}NOS$ | 192.25 | 192 |
| P Pro | $C_{12}H_{12}NOS$ | 218.29 | 218 |
| V Val | $C_{12}H_{14}NOS$ | 220.30 | 220 |
| I,L Ile.Leu | $C_{13}H_{16}NOS$ | 234.33 | 234 |
| N Asn | $C_{11}H_{11}N_2O_2S$ | 235.28 | 235 |
| Q Gln | $C_{12}H_{13}N_2O_2S$ | 249.30 | 249 |
| D Asp-OMe | $C_{12}H_{12}NO_3S$ | 250.29 | 250 |
| M Met | $C_{12}H_{14}NOS_2$ | 252.37 | 252 |
| H His+ | $C_{13}H_{13}N_3OS$ | 258.32 | 259 |
| E Glu-OMe | $C_{13}H_{14}NO_3S$ | 264.31 | 264 |
| F Phe | $C_{16}H_{14}NOS$ | 268.34 | 268 |
| K Arg+ | $C_{13}H_{18}N_4OS$ | 277.36 | 278 |
| Y Tyr | $C_{16}H_{14}NO_2S$ | 284.34 | 284 |
| W Trp | $C_{18}H_{15}N_2OS$ | 307.38 | 307 |
| K Lys | $C_{19}H_{19}N_2OS$ | 369.51 | 370 |

EXAMPLE III

Preparation of 5-Acetoxy-2-phenylthiazoles. 5-Hydroxy-2-phenylthiazolium hydrochlorides (0.001 mole) were neutralized by treatment with excess 1N sodium hydrogen carbonate ($NaHCO_3$) and extracted into ether. The extracts were dried over anhydrous $MgSO_4$ and concentrated in vacuo. The residue was dissolved in acetic anhydride (1 mL) and one drop of pyridine added. The product was concentrated in vacuo and crystallized from ligroin (b.p. 60–90). 5-Acetoxy-2-phenylthiazoles were obtained in approx. 90% yields by this method. In several instances, crystalline 5-acetoxy-2-phenylthiazoles could not be obtained, and the corresponding 5-acetoxy-2-phenylthiazolium hydrochlorides were prepared by addition of anhydrous 1N HCl in diethyl ether to the residue containing the 5-acetoxy-2-phenylthiazole. The products were characterized by LD-TOF-MS as described above.

EXAMPLE IV

Gas Chromatography/Chemical Ionization Mass Spectrometric Detection of 5-Acetoxy-2-phenylthiazoles. 5-Acetoxy-2-phenylthiazoles were also prepared on an analytical scale from 5-hydroxy-2-phenylthiazolium hydrochlorides (approx. 1 mg) by reaction with either neat acetic anhydride (1 mL) at 75° C. for 10 min. or 7:2:1 acetonitrile:triethylamine:acetic anhydride (1 mL) at 40° C. for 3 min. After cooling to room temperature, the products were dried under a stream of dry nitrogen. The residue was dissolved in 7:3 ethyl acetate:triethylamine (1 mL) to afford a solution containing approx. 1 μg/μL of product. Aloquots of product (1

μL) were analyzed by gas chromatography/mass spectrometry (GC/MS) on a Finnigan MAT ITS40 ion trap mass spectrometer. A DB-5 capillary gas chromatography column (J and W) of 30 m length (0.25 mm I.D.) provided baseline resolution of all 5-acetoxy-2-phenylthiazoles in under 10 min. with an average peak width at half height of <3 sec. Mass spectrometric detection employing methane Cl allowed detection of the analytes as 5-acetoxy-2-phenylthiazolium ions. Chemical ionization induced fragmentation also produced, to a lesser extent, the corresponding 5-hydroxy-phenylthiazolium ions. Leucine and isoleucine were differentiated by their gas chromatographic retention times. With limited optimization, all analytes were detected at or below the 1 picogram (<10 femtomole) level. The following masses were determined experimentally for 5-acetoxy-2-phenylthiazolium ions.

| 2-Phenylthiazolium Ions Detected by Gas Chromatography/Ion Trap Mass Spectrometry | | | | |
|---|---|---|---|---|
| R | Formula | 5-Hydroxy | 5-Acetoxy | 5,R-Diacetoxy |
| G Gly | C$_9$H$_8$NOS | 178 | 220 | |
| (C),(S) δAla | C$_{10}$H$_8$NOS | 190 | | |
| A Ala | C$_{10}$H$_{10}$NOS | 192 | 234 | |
| (T) δAbu | C$_{11}$H$_{10}$NOS | 204 | 246 | |
| P Pro | C$_{12}$H$_{12}$NOS | 218 | | |
| V Val | C$_{12}$H$_{14}$NOS | 220 | 262 | |
| (N) δAsn | C$_{11}$H$_{11}$N$_2$OS | 217 | 259 | |
| (Q) δGln | C$_{12}$H$_{11}$N$_2$OS | 231 | 273 | |
| I,L Ile,Leu | C$_{13}$H$_{16}$NOS | 234 | 276 | |
| N Asn | C$_{11}$H$_{11}$N$_2$O$_2$S | 235 | 277 | |
| Q Gln | C$_{12}$H$_{13}$N$_2$O$_2$S | 249 | 291 | |
| D Asp-OMe | C$_{12}$H$_{12}$NO$_3$S | 250 | 292 | |
| M Met | C$_{12}$H$_{14}$NOS$_2$ | 252 | 294 | |
| H His+ | C$_{13}$H$_{13}$N$_2$OS | 259 | 301 | 342 |
| E Glu-Ome | C$_{13}$H$_{14}$NO$_3$S | 264 | 306 | |
| F Phe | C$_{16}$H$_{14}$NOS | 268 | 310 | |
| K Arg+ | C$_{13}$H$_{18}$N$_4$OS | 278 | 320 & 362 | 362 & 404 |
| Y Tyr | C$_{16}$H$_{14}$NO$_2$S | 284 | 326 | 368 |
| W Trp | C$_{18}$H$_{15}$N$_2$OS | 307 | 349 | 391 |
| K Lys | C$_{19}$H$_{19}$N$_2$OS | 323 | 365 | 407 |

EXAMPLE V

Thiobenzoylation Method of Protein Microsequencing. The base-catalyzed thiobenzoylation of the N-terminal amino acid was achieved by reaction with S-(carboxymethyl)dithiobenzoate with the concomitant liberation of mercaptoacetic acid. The reaction proceeds efficiently only in highly polar solvents. Consequently, covalent immobilization of the sample was a necessary prerequisite to analysis. Cleavage of the N-terminal amino acid was effected with liquid trifluoroacetic acid (TFA) for 3 min. at 40° C. The required conditions are mild as compared to the Edman degradation. The 2-phenyl-5(4H)-thiazolone cleavage product exists in tautomeric equilibrium with the corresponding 5-hydroxy-2-phenylthiazole (enol) and a zwitterionic tautomer which is only present in highly polar solvents. The 5-hydroxy-2-phenylthiazoles were acetylated and analyzed by GC/MS as described above.

To demonstrate the potential of this approach to sub-picomole microsequencing, a synthetic test peptide having the sequence Val-Tyr-Asp-Ala-Arg-Tyr-Trp-Glu-Glu-Ala-His-Cys-Gly-Arg-Met-OH was analyzed. One (1) picomole of test peptide was immobilized on a Sequelon DITC membrane (MilliGen/Biosearch), and subjected to 10 cycles of thiobenzoylation degradation. The initial yield was estimated to be approximately 400 femtomoles. Only 1/20th of each sample was analyzed, owing to the limitations of the injector installed on the GC/MS system. Consequently, analytes were detected at or below the 20 femtomole level. Nevertheless, useful data was obtained for each of the first seven cycles.

I claim:

1. A method for determining the identity of an N-terminal amino acid of a polypeptide comprising the steps of:

a) attaching a polypeptide having an N-terminal amino acid to a solid support;

b) reacting said polypeptide with a thiobenzoylating reagent having the general formula:

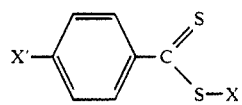

wherein X is an electron withdrawing group, and X' is a reactivity modifying substituent to form an N-thiobenzoyl polypeptide having the general formula:

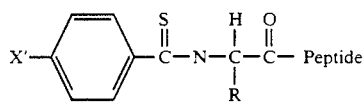

wherein R is selected from the group consisting of amino acid side chains;

c) treating the N-thiobenzoyl polypeptide with a cleavage acid to cleave the N-terminal amino acid from the remaining peptide, wherein a 4-substituted 2-phenyl-5(4H) thiazolone is formed having the following general formula:

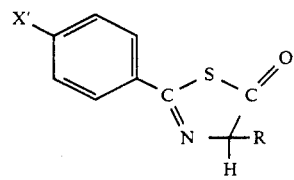

wherein X' and R are as defined above;

d) reacting the 4-substituted 2-phenyl-5(4H) thiazolone with an acetylating agent to form a 5-acyloxy-2-phenylthiazole derivative having the general formula:

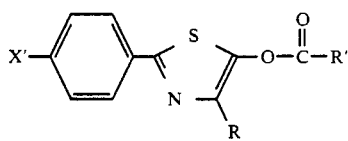

wherein R' is selected from the groups consisting of CH$_3$, CF$_3$, CF$_2$CF$_3$ and CF$_2$CF$_2$CF$_3$; and e) identifying the 5-acyloxy-2-phenylthiazole of step d.

2. The method of claim 1 wherein said thiobenzoylating reagent of step b is S-(carboxymethy)dithioacetate having the formula

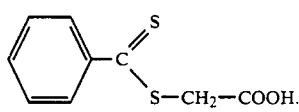

3. The method of claim 1 wherein the acetylating agent is selected from the group consisting of acetic anhydride, trifluoroacetic anhydride (TFAA), pentafluoropropionic anhydride (PFAA), heptafluorobutyric anhydride (HFBAA) and combinations thereof.

4. The method of claim 1 wherein X is selected from the group consisting of —CH$_2$COOH, —CH$_2$CN, —CH$_2$COOCH$_3$ and —CH$_2$OCH$_3$.

5. The method of claim 1 wherein X' is selected from the group consisting of —NO$_2$, —CN, —CH$_3$, —OCH$_3$ and —SO$_3$.

6. The method of claim 1 wherein R' is selected from the group consisting of CH$_3$ and CF$_3$.

7. The method of claim 1 wherein the thiobenzoylation reaction occurs in the presence of 1% to 10% triethyl amine (TEA) or N-methylmorpholine in a solution containing up to 50% organic alcohol or acetonitrile at a temperature from 40° to 75° C., said solution being applied to the peptide at a prescribed rate of about 25-250 μl per minute.

8. The method of claim 7 wherein the acetylating agent is a 7:2:1 ratio combination of acetonitrile:TEA:acetic anhydride.

9. The method of claim 1 wherein the cleavage acid is selected from the group consisting of a perfluorinated carboxylic acid and an anhydrous hydrochloric acid.

10. The method of claim 9 wherein the cleavage acid is an anhydrous hydrochloric acid which is selected from the group consisting of 4N HCl in dioxane and 1N HCl in diethyl ether.

11. The method of claim 9 wherein the cleavage acid is a perfluorinated carboxylic acid which is selected from the group consisting of a trifluoroacetic acid (TFA), pentafluoropropionic acid, and heptafluorobutyric acid.

12. The method of claim 11 wherein the perfluorinated carboxylic acid is trifluoroacetic acid (TFA) in liquid or vapor form.

13. The method of claim 1 further comprising the step of drying the 5-acyloxy-2-phenylthiazole by evaporation in vacuo or under a stream of argon or nitrogen gas and then dissolving the dried thiazole in an aprotic organic solvent.

14. The method of claim 13 wherein the aprotic organic solvent is selected from the group consisting of ethyl acetate, hexane and acetonitrile and contains up to 30% by volume TEA.

15. The method of claim 1 wherein the identifying step occurs in a gas chromatography/mass spectrometer equipped with chemical ionization detection by introducing the 5-acyloxy-2-phenythiazole into an ionization chamber of the mass spectrometer wherein it collides with reagent gas ions to produce, by proton transfer, 5-acyloxy-2-phenylthiazolium ions of the general formula:

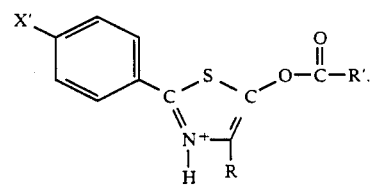

16. The method of claim 15 wherein the thiazolium compounds are identified by capillary gas chromatography based upon the GC retention time of the compounds compared with a standard.

17. The method of claim 15 wherein the chemical ionization detection occurs in a detector using a gas selected from the group consisting of ammonia, methane, methanol and isobutane.

18. The method of claim 17 wherein the gas is isobutane.

* * * * *